US 6,558,242 B2

(12) United States Patent
Veldkamp et al.

(10) Patent No.: US 6,558,242 B2
(45) Date of Patent: May 6, 2003

(54) METHOD AND APPARATUS FOR REMOVING FAT FROM MEAT CUTS

(75) Inventors: Brent M. Veldkamp, Cumming, IA (US); R. Thomas Seaberg, Des Moines, IA (US); Don D. Holms, West Des Moines, IA (US); Doug McCloskey, Altoona, IA (US)

(73) Assignee: Townsend Engineering Company, Des Moines, IA (US)

( * ) Notice: Subject to any disclaimer, the term of this patent is extended or adjusted under 35 U.S.C. 154(b) by 0 days.

(21) Appl. No.: 09/835,748

(22) Filed: Apr. 16, 2001

(65) Prior Publication Data

US 2001/0036807 A1 Nov. 1, 2001

Related U.S. Application Data

(63) Continuation-in-part of application No. 09/552,396, filed on Apr. 19, 2000.

(51) Int. Cl.$^7$ .............................................. A22C 17/16
(52) U.S. Cl. ...................................... 452/134; 452/127
(58) Field of Search ................................ 452/134, 127, 452/150; 99/486, 489, 537

(56) References Cited

U.S. PATENT DOCUMENTS

| 3,237,664 | A | * | 3/1966 | Macy et al. ................. 452/134 |
| 3,613,154 | A | | 10/1971 | Townsend |
| 3,789,456 | A | | 2/1974 | Doerfer et al. |
| 4,189,806 | A | * | 2/1980 | Van Heyningen ........... 452/134 |
| 4,201,302 | A | * | 5/1980 | Roth .......................... 209/577 |
| 4,209,878 | A | | 7/1980 | Albert |
| 4,246,837 | A | | 1/1981 | Chenery |
| 4,628,806 | A | | 12/1986 | Murphy |
| 4,970,755 | A | | 11/1990 | Leblanc |
| 4,979,269 | A | | 12/1990 | Norrie |
| 5,090,939 | A | | 2/1992 | Leblanc |
| RE33,904 | E | * | 4/1992 | Rudy et al. ................. 452/150 |
| 5,236,323 | A | * | 8/1993 | Long et al. ................. 452/127 |
| 5,324,228 | A | * | 6/1994 | Vogeley, Jr. ................ 452/158 |
| 5,334,084 | A | * | 8/1994 | O'Brien et al. ............. 452/157 |
| 5,350,334 | A | * | 9/1994 | Holms ........................ 452/127 |
| 5,429,548 | A | | 7/1995 | Long et al. |
| 5,476,417 | A | | 12/1995 | Long et al. |
| 5,738,577 | A | | 4/1998 | Long |
| 6,088,114 | A | * | 7/2000 | Richmond et al. .......... 356/417 |
| 6,118,542 | A | * | 9/2000 | Andersen et al. ........... 356/445 |
| 6,129,625 | A | | 10/2000 | Cate et al. |
| 6,193,596 | B1 | * | 2/2001 | Adcock ....................... 452/180 |

FOREIGN PATENT DOCUMENTS

| EP | 0324522 A1 | * | 7/1989 |
| EP | 0 402 877 B1 | | 12/1990 |
| EP | 0 484 933 B1 | | 3/1994 |

* cited by examiner

Primary Examiner—Peter M. Poon
Assistant Examiner—David Parsley

(57) ABSTRACT

A method and apparatus for removing a portion of fat from meat cuts involves placing a meat cut on a longitudinal conveyor, pressing sensor probes into the meat cut to measure the relative thickness of fat and the location of lean in the meat, and then withdrawing the sensor probes from the meat. An electronic signal is transmitted from the sensor to a controller along with an encoder signal to determine the depth from the outer lower surface of the meat cut through a layer of fat in the meat to a layer of lean in the meat. Data taken from the foregoing step determine the desired position of the blade, which removes the appropriate amount of fat to be removed from the meat cut.

13 Claims, 12 Drawing Sheets

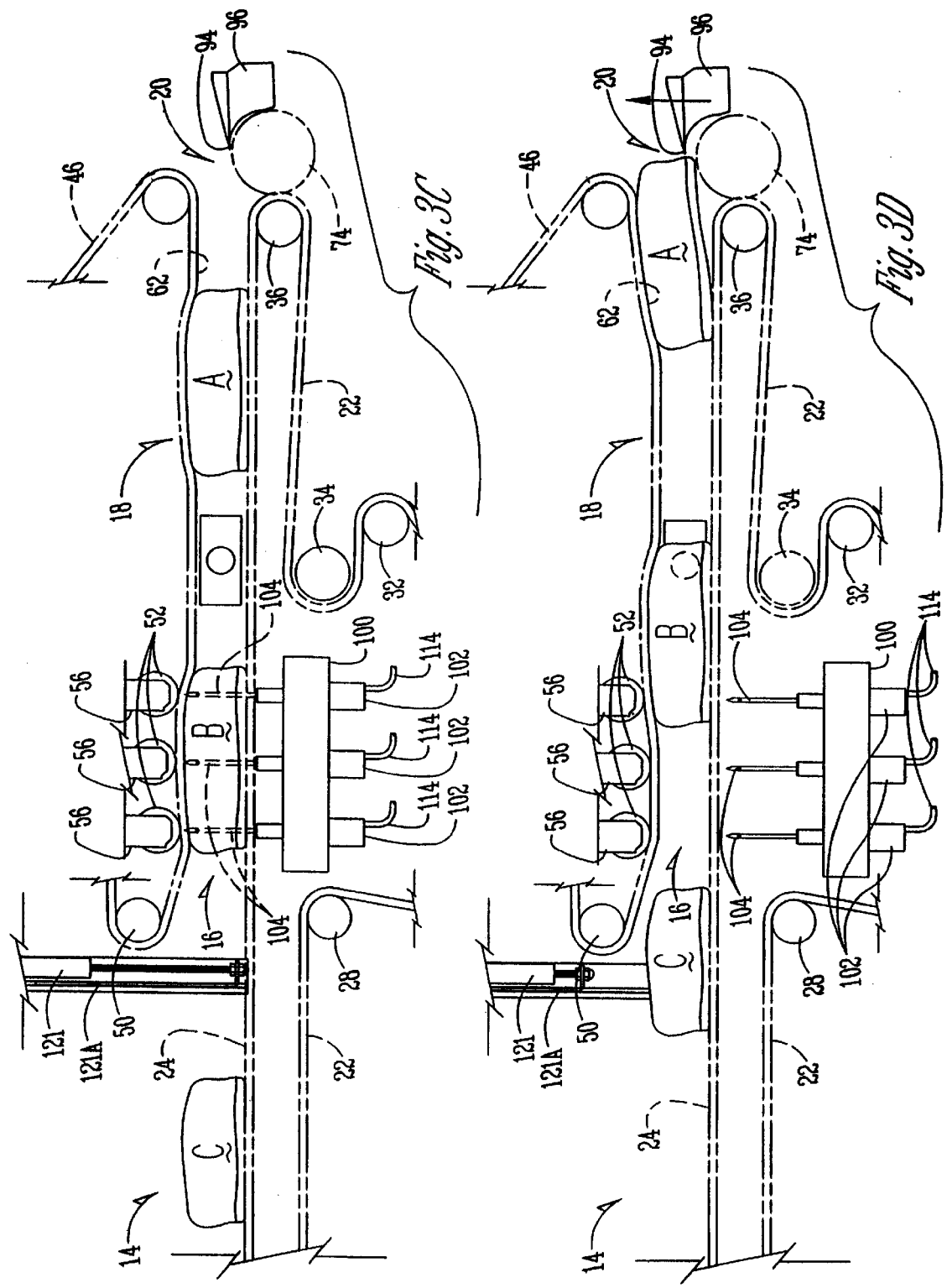

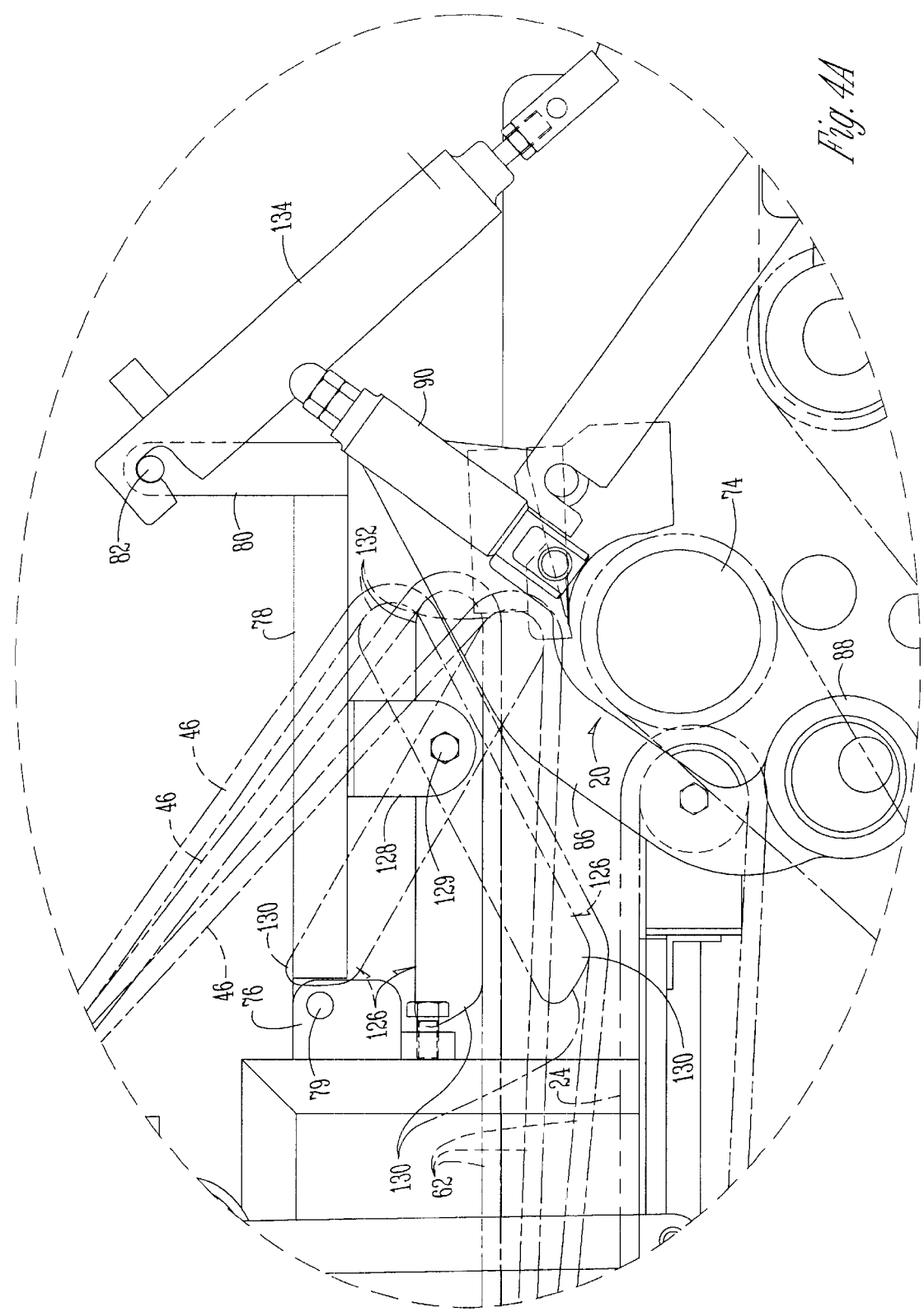

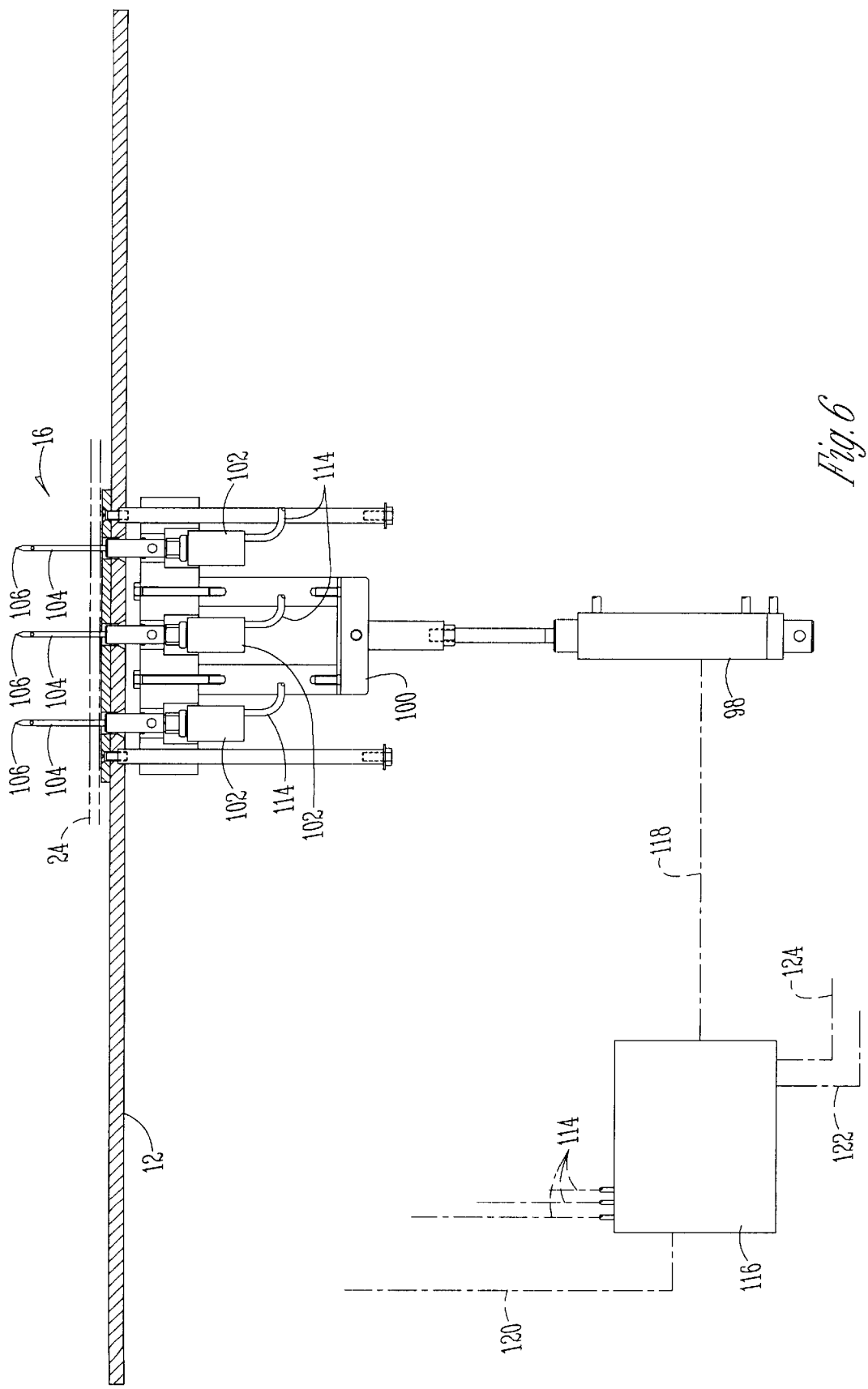

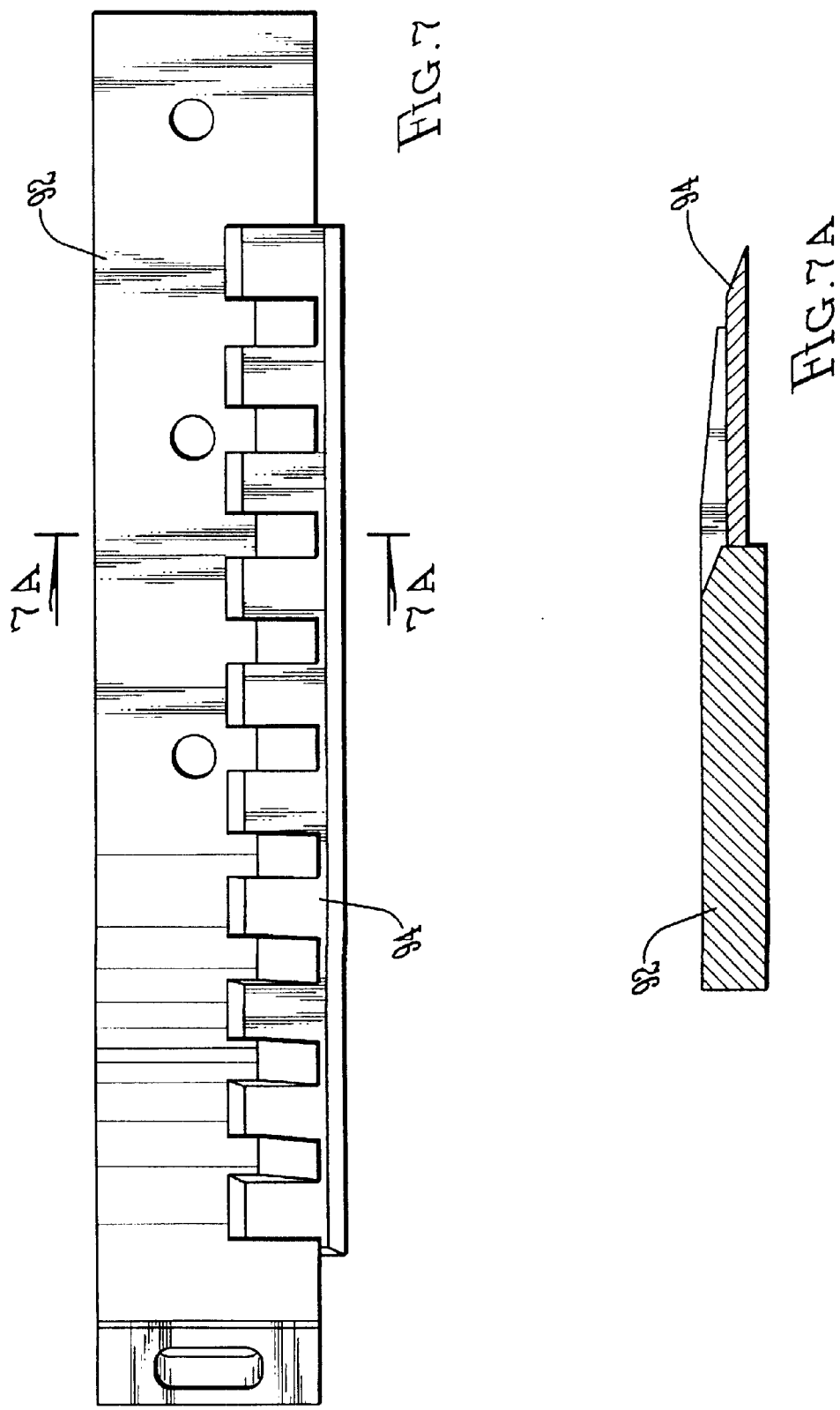

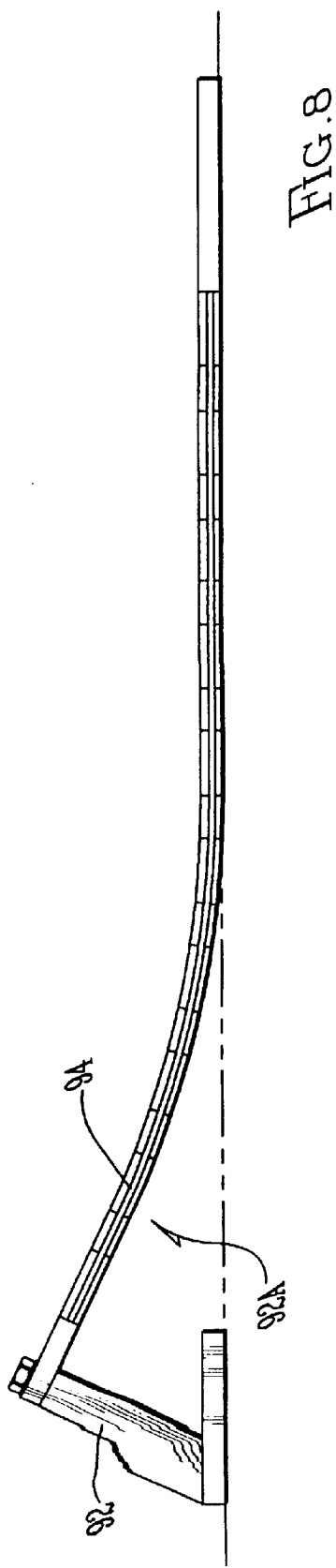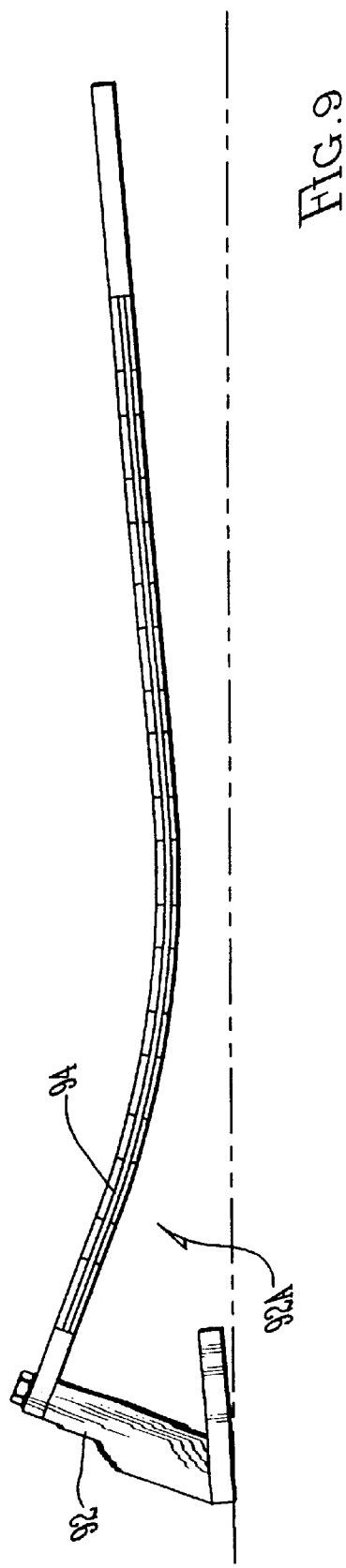

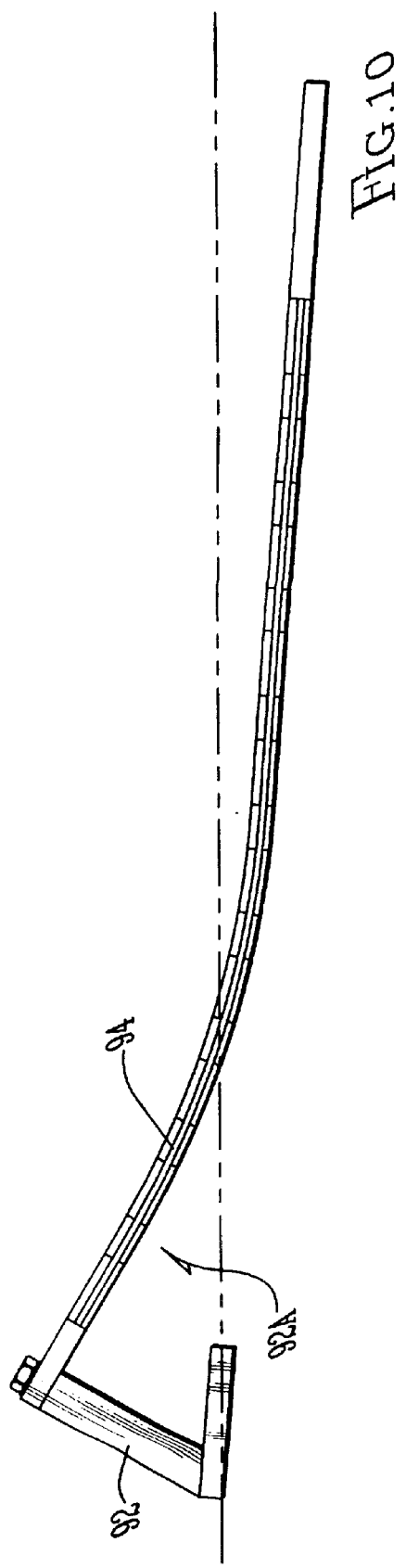

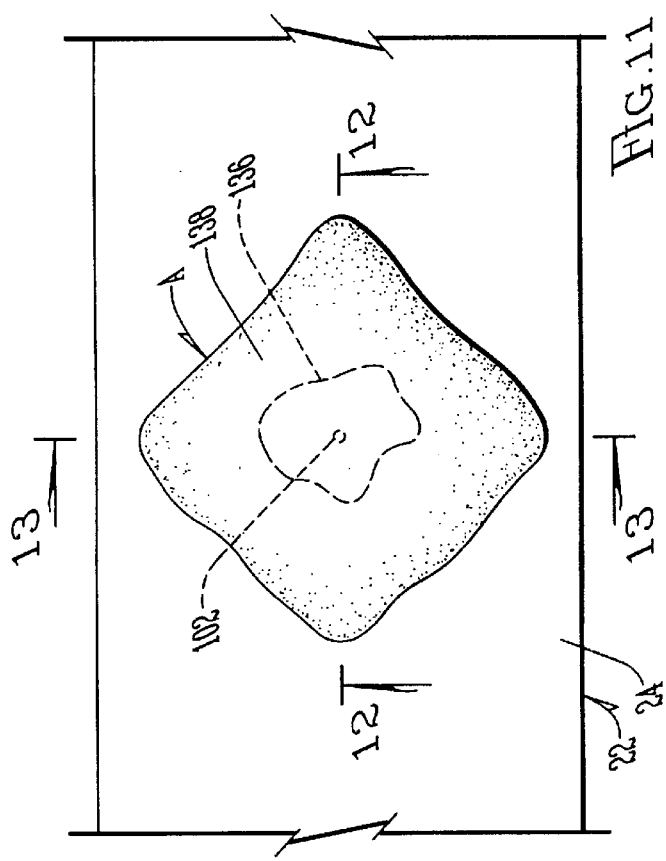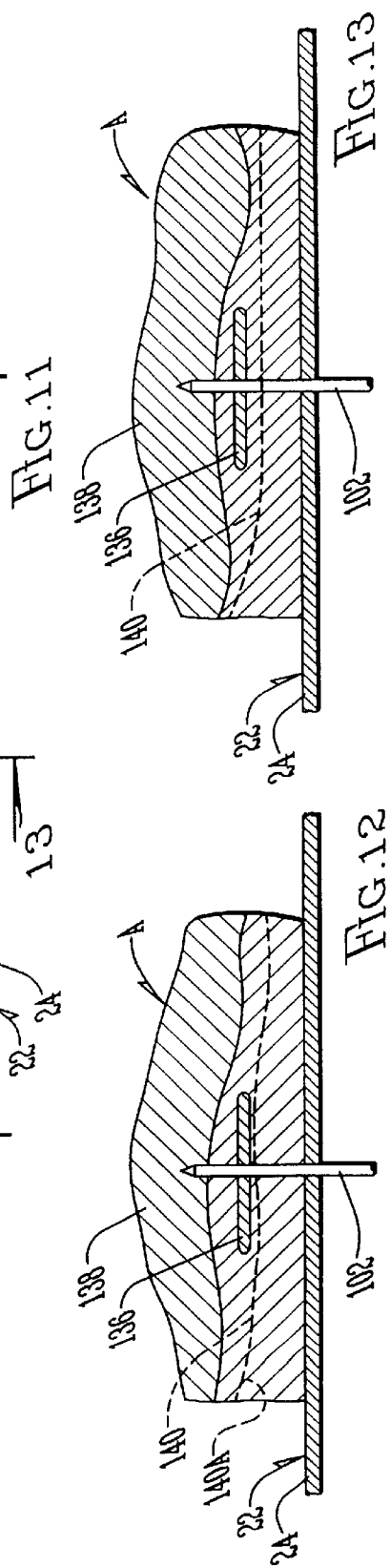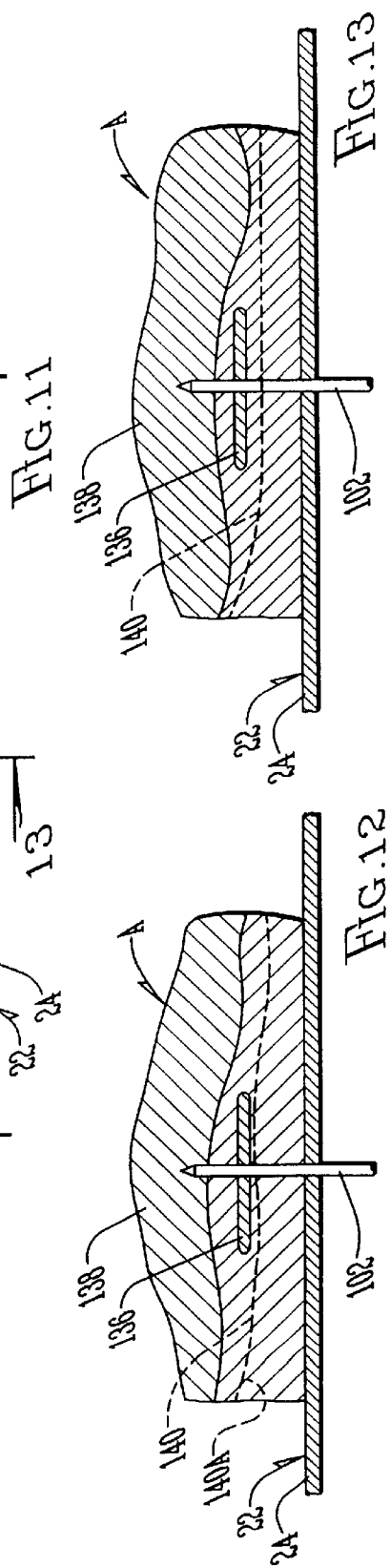

METHOD AND APPARATUS FOR REMOVING FAT FROM MEAT CUTS

CROSS REFERENCE TO A RELATED APPLICATION

This application is a continuation-in-part of Ser. No. 09/552,396 filed Apr. 19, 2000.

BACKGROUND OF THE INVENTION

In the production of processing meat cuts, such as pork butts, existing specifications require that sufficient fat be removed from the butt to expose six to eight square inches of lean meat, while leaving ⅛th to ¼th of an inch fat cover on the remaining curved surface of the meat cut.

Existing machines and methods for achieving the above specification involve safety hazards and inaccurate cutting which results in waste of meat product. Further, more than one trimming operation is normally required to achieve the needed specification. Existing processes are labor intensive.

Until now, the process of removing an optimal amount of fat from meat cuts such as pork butts has required a person who makes repeated cuts until the desired amount of lean meat is exposed. Often this results in waste, as it is impossible to tell without cutting into it at what depth the lean starts and the fat stops.

Previous attempts at automating this process have met with failure because of the variation in fat cover on the meat cuts. The fat cover on meat cuts typically has a layer of lean running through it, which starts about halfway between the neck and the back which is called the false lean. The fat cover is normally thinnest at the neck edge and fattest at the back edge. It is customary when preparing such meat for sale to remove a wedge-shaped piece of fat in order to expose the "false lean". Typically in the industry, enough fat should be removed to expose at least six square inches of lean meat while leaving ⅛th to ¼th of an inch of fat cover on the remaining surface.

It is therefore a principal object of this invention to provide an apparatus for removing a portion of fat from meat cuts which is safe, accurate, and efficient both from a standpoint of time and labor involved.

It is a further object of the invention to provide for the photometric determination of the layers of fat and lean within individual pieces of meat for the purpose of guiding the automated removal of optimal amounts of unwanted material by means of an optical device located within a specially constructed probe.

It is a further object of this invention to use either a stationary or movable blade for fat removal in accordance with a predetermined cutting profile.

These and other objects will be apparent to those skilled in the art.

SUMMARY OF THE INVENTION

A method for removing a portion of fat from meat cuts involves placing the meat on a longitudinal conveyor, pressing sensor probes into the meat to measure the thickness of fat and the location of lean therein, and then withdrawing the sensor probes therefrom. An electronic signal is transmitted from the sensor probes to a controller and encoder to determine the depth from the outer lower surface of the meat through a layer of fat therein to a layer of lean. Data taken from the foregoing step determine the desired position of the cutting blade. A predetermined amount of fat is thereupon cut from the meat by the blade. The method is used to determine in meat the layer thicknesses by recording at uniform intervals during the penetration into the meat properties of the reflected light. These properties are mapped against the distance traveled by the probe will show segment thickness.

In an alternate form of the invention, data from a sensor is sent to the control mechanism of the cutting blade. This blade may then be moved according to the information provided by the sensor. If a sensor is not used, then the operator determines the fat thickness of the butts he will be removing from and sets the blade at a position.

An apparatus for removing a portion of fat from meat cuts includes a frame and at least one sensor probe including fiber optics to permit scanning of the interior of a meat cut penetrated by the probe. Power for moving the probe into the meat is mounted on the frame along with a skinning blade mounted in a path of movement of a meat cut on the frame.

A controller on the frame takes data from the sensor probe and determines the linear depth of fat material on the meat cut and lean material in the meat cut. The controller then determines the operating position of the blade and positions the blade to effect the removal of the desired amount of fat. The cutting height of the blade is determined by the sensor.

More specifically, a meat piece is conveyed on a conveyor belt towards the cutting device. The frame supports the probes beneath the conveyor of the meat. As soon as the meat rides over the probe path, the meat pauses, an air cylinder activates and the probes penetrate the meat. The optic fibers for reception and transmission of the signals are threaded through the probes. The probes have a probe window at the distal end. An LED sends light through a first set of fibers in the probes. The receiving signals picked up by the receiving optical fibers send a message to the controller which analyzes the signals. The probes take measurements while they are engaged with the meat piece both on the up and the down stroke. After they are withdrawn and the meat piece travels further into engagement with the skinning mechanism. The signal analysis generates a message, which is used by the blade control device to raise or lower the blade from the pulling surface of the skinning mechanism, resulting in the removal of a piece composed primarily of fat.

The difference in reflected light properties between the fat and lean muscle is distinct enough that a simple probe containing optical fibers can easily distinguish between them. This information is relayed to a controller which controls the motion of a blade.

The controller makes a determination based on the registration of a large number of reflected light properties at intervals of depth in the piece of meat. In addition, all values are inserted into a suitable equation or equation system, which is a multi-variable algorithm for the calculation of layer thicknesses.

The multivariable algorithm may include a preset offset distance which accounts for the distance between the cutting blade and toothroll in the minimum cutting position, and a variable offset which can be modified by the operator to customize this product appearance according to this customer specifications.

In addition, the algorithm may include other variables to vary the desired cutting depth at different times during the cut. For example, the cutting depth may be decreased during the first one-third of the meat to increase the resulting fat depth on the finished product. During the second one-third of the meat the cutting depth may be at the calculated depth. During the last one-third of the meat, the cutting depth may be increased to remove more fat in that area.

The cutting device includes a toothroll, shoe and curved blade holder. The blade holder is fastened to a short section of the shoe. The blade holder provides the desired curved cut, while the shoe/toothroll provides the means to pull the meat through the blade. The blade height adjusting mechanism is actuated electromechanically. The toothroll and exit conveyor drive rotate continuously. The conveyor system must move the meat through the stations, and present it to the cutting device. It indexes, so the meat is stationary when being probed. The conveyor belt is modular to ensure positive indexing. The stations are marked by blue segments on the belt. The stations are a set distance apart. During indexing, the belt accelerates for a set distance, moves at a constant speed a set distance (the approximate length of the meat cut), then decelerates a set distance. The maximum, constant speed of the conveyor is set below the surface speed of the toothroll while the meat is moving through the cutting device. The conveyors must hold the meat securely during probing, and maintain its position through the cutting device so that the depth cut is consistent with the depth measured by the probe. A pivoting, flat top plate positioned just ahead of the blade alternately presses the front end and the back end of the meat into the shoe/toothroll/blade to ensure that the meat gets a good start and finish. An alternate pivoting, curved top plate is used to press the outside edges of the meat into the toothroll for better cuttinq performance.

In an alternate form of the invention, once the blade has been set the meat advances on the conveyor into contact with the blade. The blade mechanism then follows a predetermined arcuate path. This path is based on the measured fat thickness or operator setting and reflects the statistical average of fat covering the butt, which has been determined by the inventors.

The cutting device includes a toothroll, shoe and curved blade holder. The blade holder is curved to cut an arcuate line through the butt perpendicular to the direction of travel. The blade holder is fastened to a short section of shoe. The blade holder provides the desired curved cut, while the shoe/toothroll provides the means to pull the meat through the blade. The blade height adjusting mechanism is actuated electromechanically. This allows the thickness of the fat plate removed to vary from front to back and side to side. The gripper roll and exit conveyor drive rotate continuously.

The infeed conveyor system must move the meat through the stations and present it to the cutting device. The infeed conveyor at its maximum, constant speed is set slower than the gripper roll. This speed differential helps to manipulate the meat piece over the shoe and blade system for accurate fat removal. The speed differential preserves the profile of the meat by compensating for any resistance at the blade.

BRIEF DESCRIPTION OF THE DRAWINGS

FIGS. 3A–3D are schematic elevational views showing the sequential steps of the method of this invention as practiced on the apparatus of this invention;

FIG. 4A is an enlarged scale side elevational view of the cutting station as shown in FIGS. 1 and 2;

FIG. 6 is an enlarged scale side elevational view of the apparatus at the sensor station of this invention;

FIG. 7 is a plan view of the blade holder and blade of FIG. 4;

FIG. 7A is an enlarged scale sectional view taken on line 7A–7A of FIG. 7;

FIG. 8 is a partial rearward elevational view of the blade and blade holder of FIG. 7 when the blade holder is in a horizontal position;

FIGS. 9 and 10 are similar to FIG. 8 but show the apparatus tilted in opposite directions under different conditions;

FIG. 11 is a plan view of a piece of meat on a conveyor;

FIG. 12 is a sectional view taken on line 12–12 of FIG. 11; and

FIG. 13 is a sectional view taken on line 13–13 of FIG. 11.

DESCRIPTION OF THE PREFERRED EMBODIMENT

Figure 1:
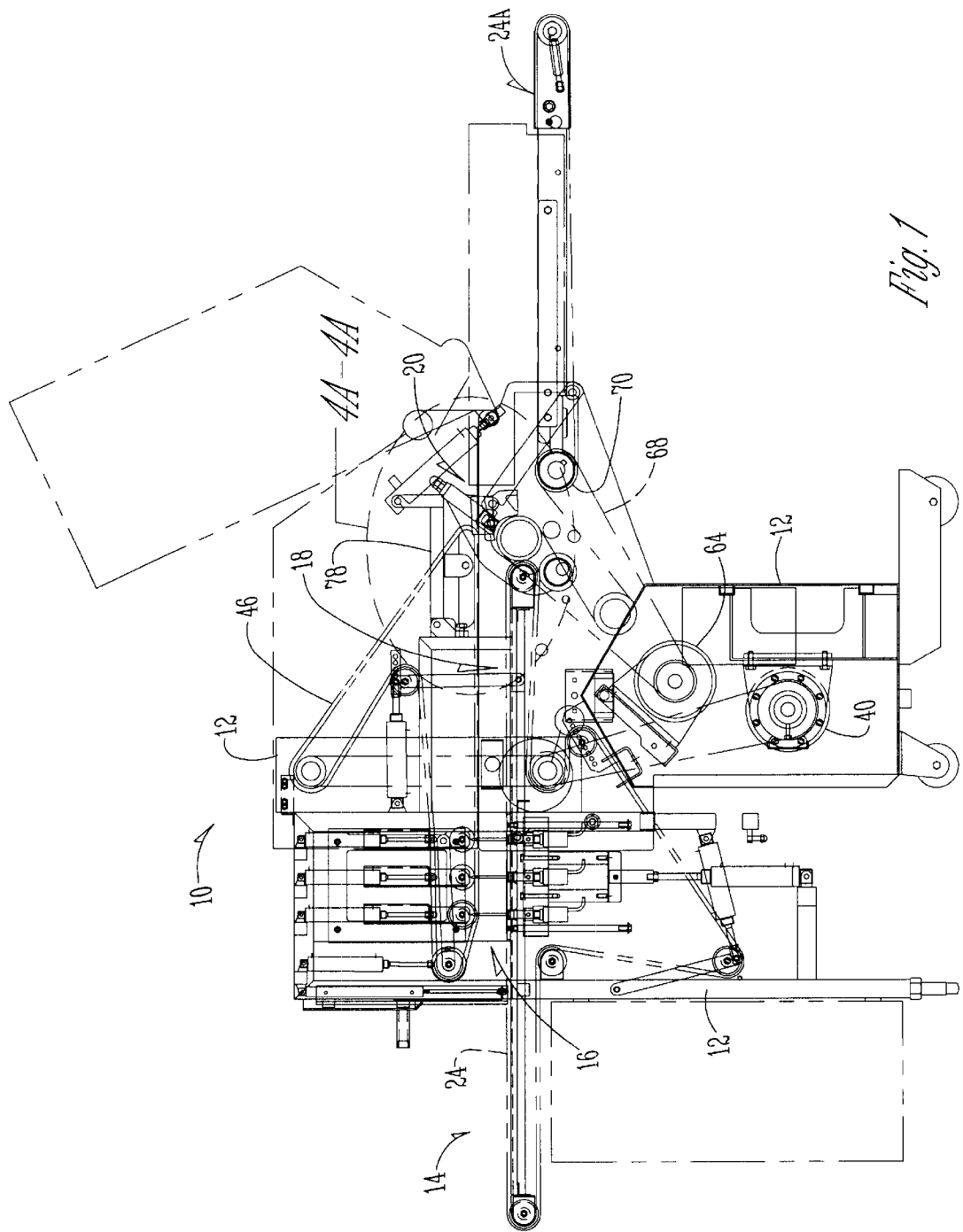
FIG. 1 is a side elevational view and partial sectional view of the apparatus of this invention.

The machine 10 has a frame 12, (FIG. 1), with a loading station 14, a probing station 16, a waiting station 18, and a skinning station 20 (FIGS. 3A–3D).

Figure 2:
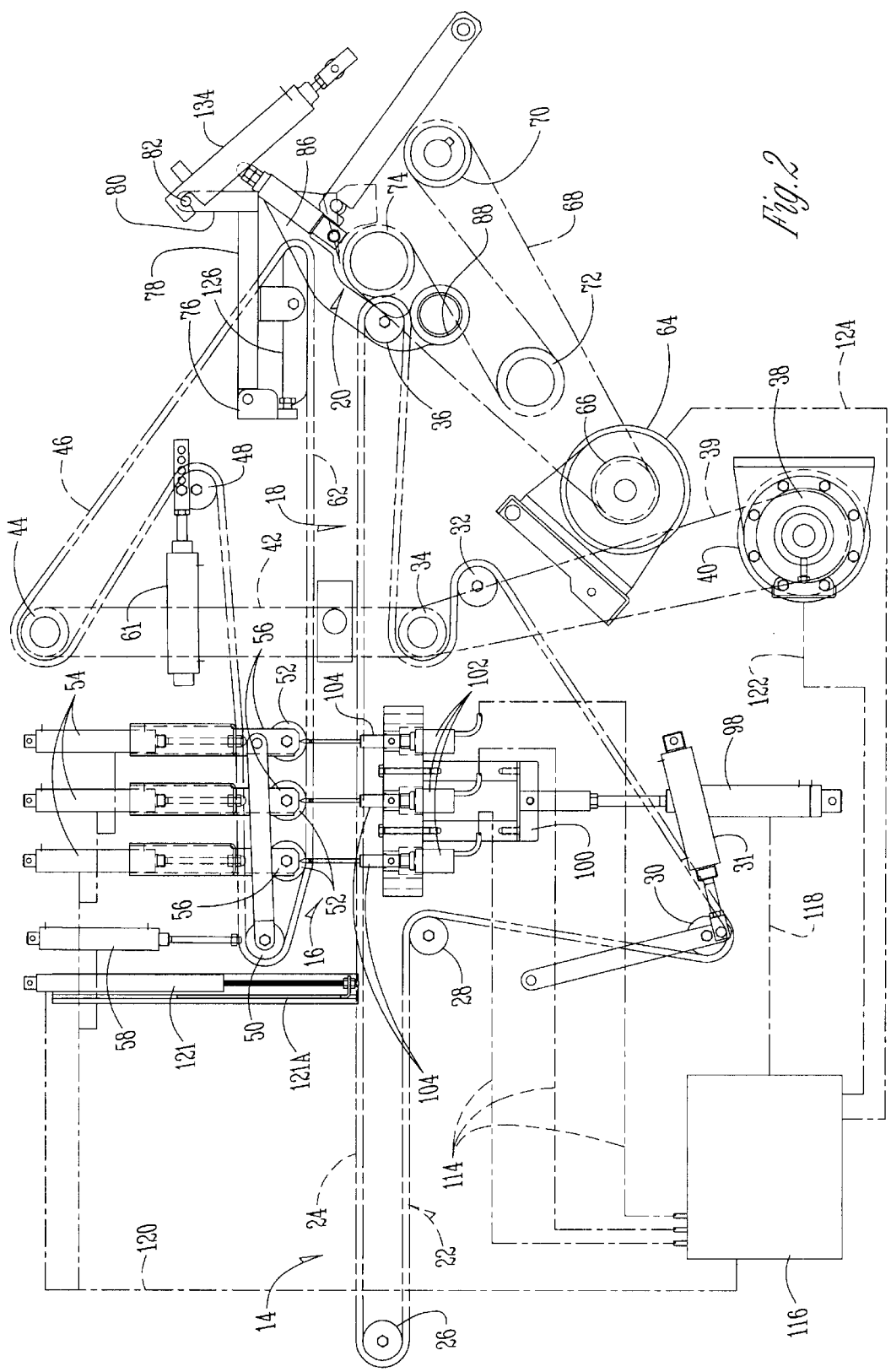
FIG. 2 is an enlarged scale layout of the power train of the apparatus of FIG. 1.

With reference to FIG. 2, a conveyor belt 22 is mounted on frame 12 and has a top horizontal portion 24. A horizontal transverse roll 26 is mounted adjacent the loading station 14 to support and reverse the direction of conveyor belt 22. The belt 22 then extends to roll 28 and extends therearound and departs in a downwardly direction towards roll 30. A conventional piston-belt-type tightener 31 is associated with roll 30 to selectively tighten or change the attitude of belt 22.

The belt 22 then departs roll 30 and extends upwardly and forwardly to roll 32 which is slightly below and forwardly of roll 34. The belt extends around roll 32 and thence rearwardly and then again forwardly as it extends around roll 34. The belt then extends to forward roll 36 and departs roll 36 back in a horizontal direction towards the point beginning at roll 26. A motor 38 (FIG. 2) is mounted on frame 12 and is connected by belt 39 to the roll and drive pulley 34 via pulley 40 on the motor.

With reference to the upper portion of FIG. 2, a chain 42 extends from roll and drive pulley 34 upwardly around a roll and drive pulley 44. A conveyor belt 46 extends around roll 44 and departs therefrom in a forwardly and downwardly direction to extend around roll 48. The belt 46 then extends rearwardly to extend around roll 50, and departs roll 50 in a forwardly horizontal direction. Belt 46 engages a plurality of rolls 52 which are mounted on the lower end of piston assemblies 54 which are mounted on downwardly extending brackets 56. Air piston 58 is parallel to the vertical air pistons 54 and is operatively connected to roll 50. Pistons 54 and 58 serve to raise and lower the belt 46 with respect to the horizontal portion 24 of belt 22 which extends thereunder. Belt 46 then extends forwardly from rolls 52 to extend around plate 126, whereupon the belt then extends rearwardly and upwardly to its point of beginning at roll 44. A conventional piston-belt tightener 61 (FIG. 2) is associated with roll 48 to facilitate the adjustment of the tension on conveyor belt 46. Roll 48 serves also as a pivot point for the upward and downward movement of the belt 46 by the pistons 54 and 58. The lower horizontal train of belt 46 as seen in FIG. 2 is identified by the numeral 62.

A motor 64 is mounted on frame 12, (FIG. 2), and has an output drive pulley 66. A belt 68 extends from pulley 66 and extends forwardly and upwardly to extend around pulley 70. The belt 68 then extends rearwardly and downwardly around pulley 72, and thence upwardly and forwardly around a drive pulley (not shown) on gripper roll 74 which is a part of the skinning station 20 as will be discussed hereafter.

Figure 4:
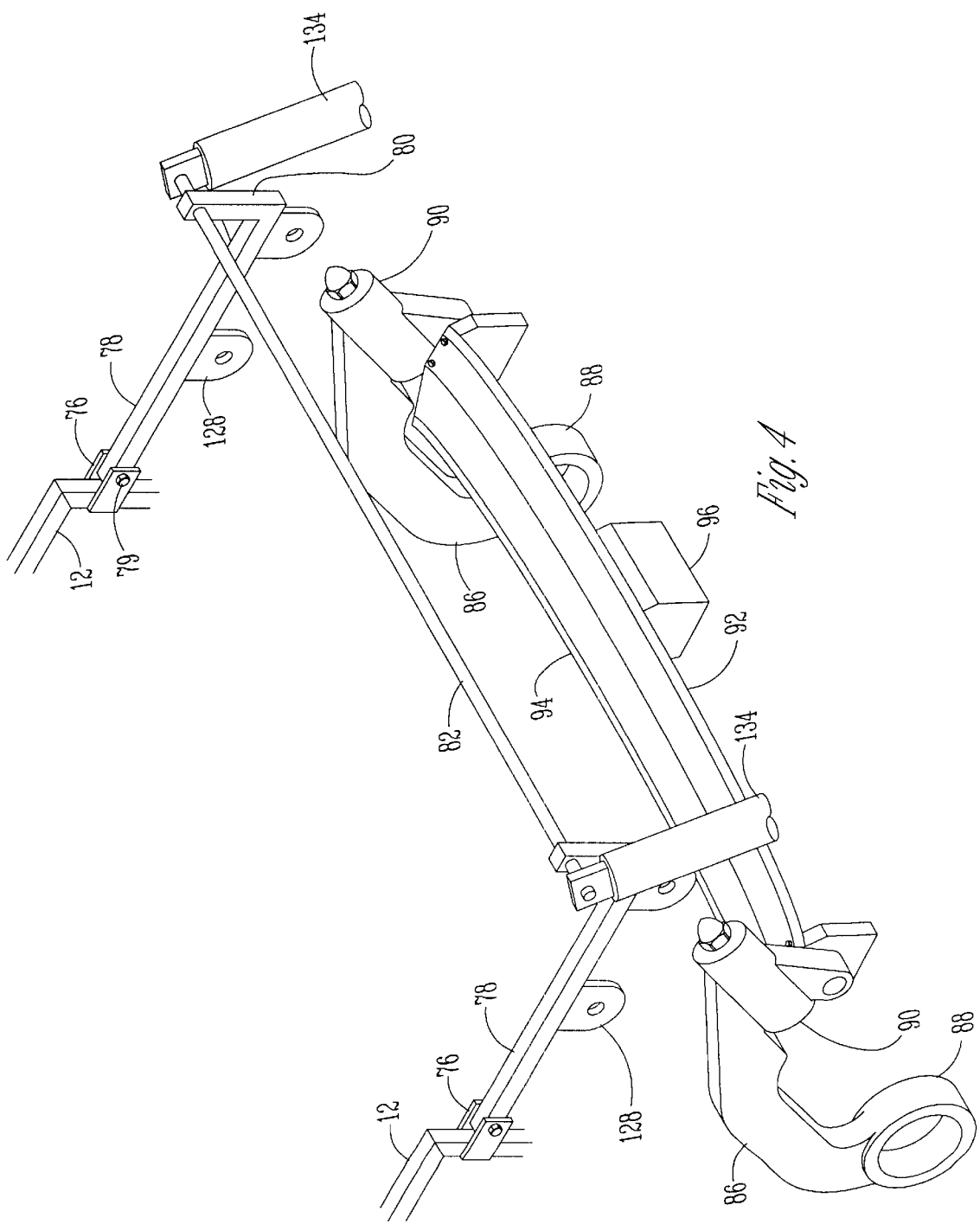
FIG. 4 is an enlarged scale perspective view of the cutting station of the device in FIG. 1.

Brackets 76 (FIG. 4) are spaced apart and are secured to frame 12 and are pivotally secured to arm 78 by the rearward ends of the arms through the function of conventional connecting pins 79. A vertical arm segment 80 extends upwardly from the forward end of the arm 78 (FIGS. 2 and 4). A transverse rod 82 extends between the upper ends of arm segments 80. Separate springs 134 are secured to the rod 82 and extend forwardly to frame 12 to yieldingly prevent the upward pivotal movement of arms 78 on pins 79.

A pair of control arms 86 (FIG. 4) are attached at their lower ends to sleeve 88 (FIG. 2) which are mounted on rotatable cams (not shown) which can raise or lower the control arms. Shoe mounts 90 are an integral part of arms 86 and conventionally are connected to the ends of the shoe 96. (FIG. 4). A blade 94 (FIGS. 3C and 3D) is secured to the blade holder 92 and shoe 96 and is conventionally associated with arcuate-shaped shoe 96 to perform the skinning operation (FIGS. 3C and 3D).

Figure 5:
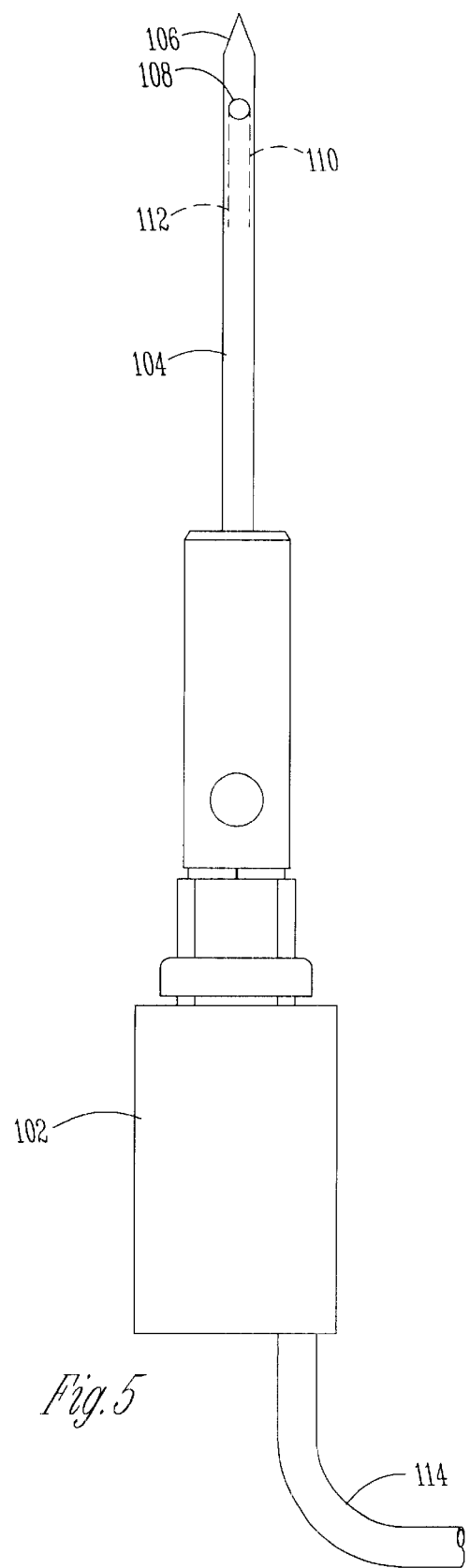
FIG. 5 is an elevational view at an enlarged scale showing one of the probe sensors.

As shown in FIG. 2, a piston assembly 98 is shown in the lower portion of that figure and is vertically disposed and is operatively connected to bracket 100. Three probe sensors 102 are vertically disposed on bracket 100 and extend upwardly therefrom and terminate in elongated probe spikes 104 (FIGS. 5 and 6). The spikes terminate at their upper ends in points 106. Each spike has a window opening 108. As shown in FIG. 5, two sets of optical fibers 110 and 112 extend through probes 102 and spikes 104 and terminate immediately adjacent the window opening 108. Optical fibers 110 are connected to a source of light in the sensor 102 to illuminate the area just outside the spike and outside the window opening 108. Optical fibers 112 have the ability to receive light that is reflected from the lean and fat portions of the meat cut being treated. The light coming from fibers 110 and reflected onto the fibers 112 from the lean and fat surfaces are returned to sensor 102 which sends a signal through lead 114 (FIG. 5) to a controller 116 (FIG. 2) including a computer. With reference to FIGS. 2 and 6, a lead 118 connects controller 116 with the piston assembly 98. Lead 120 extends from controller 116 to a slidable door 121/A and linear actuator 121 (FIGS. 2 and 3C) located just forwardly of loading station 14. Lead 120 also connects controller 116 to pistons 54 and 58. Lead 122 connects controller 116 with motor 38 (FIG. 2). Lead 124 connects controller 116 with motor 64.

With reference to FIG. 4A, a top feed plate 126 of rectangular and generally flat construction is rotatably supported by ears 128 on arm 78 (FIG. 4). An encoder (not shown) measures the position of the probes and transmits this measurement to the controller. Pins 129 effect the pivotal connection between plate 126 and the ears 128. Feedplate 126 has a leading end 130 and a trailing end 132. A spring cylinder 134 has an upper end that hooks on rod 82 and a lower end secured to the frame 12 and serves to hold feedplate 126 down on the meat cut.

The feedplate 126 is normally in the horizontal position shown by the solid lines in FIG. 4A. The lead end 130 pivots upwardly as the meat product endeavors to pass thereunder on conveyor 24. This causes the trailing end 132 to move to a level lower than the pin 129 whereupon it exerts force on the meat product as that product moves into contact with the gripping roll 74 and the blade 94. The continued longitudinal movement of the meat towards the blade then causes the meat product to push upwardly on the depressed trailing end 132 which causes the plate 126 to move to the position shown in FIG. 4A where the end 130 is depressed or lowered. The engagement of the product by the lower end portion 130 of the plate member serves to exert additional longitudinal boost to the meat product as it is moving upwardly and over the blade 94 and gripping roll 74 at the skinning station 20.

In operation, a meat cut A (FIG. 3A) is placed on the conveyor belt 22 at the loading station 14. The controller 116 has the ability to index the movement of conveyor 22, and the conveyor is motionless at this point in time. The door 121 is in an open position. The bracket 100 is in its lower position shown in FIG. 3D so that the probe spikes 104 are withdrawn and the points 106 of the spikes 104 are at a level below the lower horizontal portion 24 of belt 22.

Figure 3A:
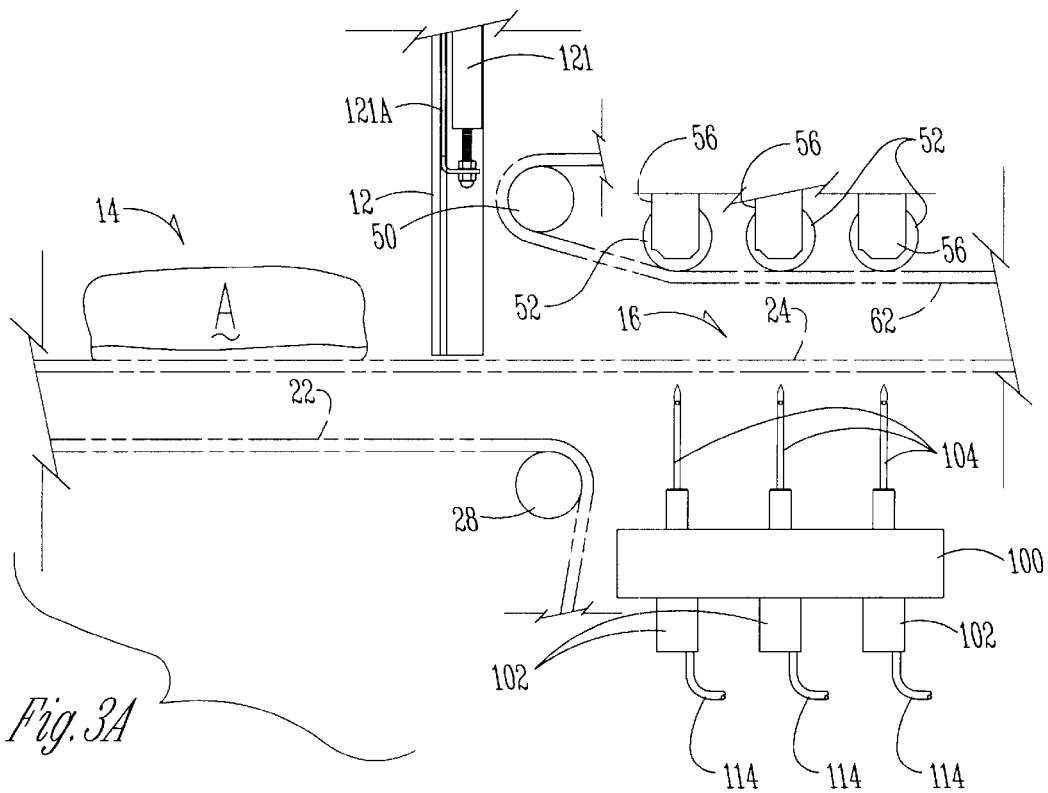
Figure 3B:
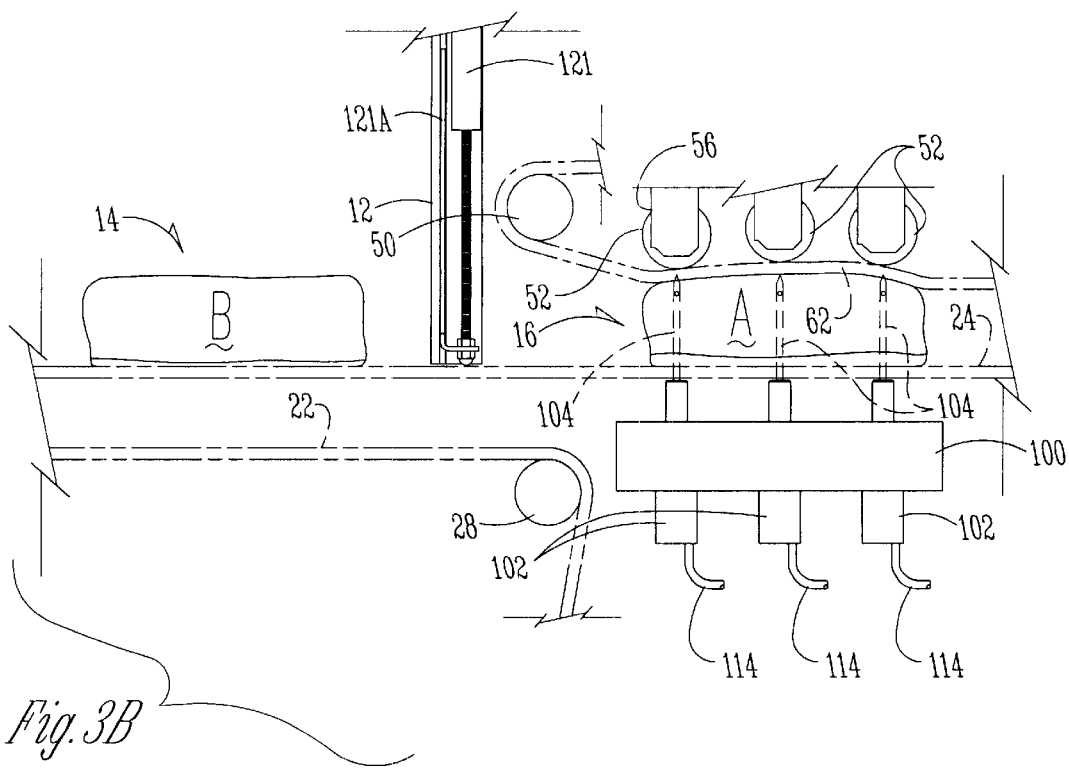

The controller 116 thereupon actuates motor 38 to cause conveyor belt 22 to advance in a clockwise direction as seen in FIG. 2 whereupon the meat cut A is moved to the probing station 16 (FIG. 3B). The controller then closes door 121A, and actuates the piston assembly 98 which causes the bracket and sensors 102 to rise whereupon the probe spikes 104 penetrate the meat cut A as shown in FIG. 3B. The pistons 54 and 58 are also actuated by the controller 116 to press down on the meat cut A as shown in FIG. 3B while the probe spikes 104 are penetrating the meat A. At the same time, meat cut B can be placed on the loading station 14.

The probe spikes move quickly upwardly and thence downwardly out of the meat product. The sensor 102 works in the manner described and permits the optical fibers 112 to receive the reflected light from optical fibers 110 through the window opening 108, with the reflected light having varying properties depending on whether the light is reflected from fat or lean meat. A signal from the reflected light through fiber optics 112 is transmitted through line 114 to controller 116 and the encoder (not shown) so that the relative thickness of the fat and lean meat is determined by the controller. Obviously, the conveyor 22 is motionless during the time when the meat cut A is penetrated by the probe spikes 104 at the probing station depicted in FIG. 3B.

The probe spikes 104 move quickly into and out of the meat cut and assume the position generally shown in FIG. 3A at a point below the conveyor belt 22. The controller 116 then opens the door 121, and advances the conveyor belt 22 to the position shown in FIG. 3C where the meat cut A is moved to the waiting station 18, and the meat cut B is moved from the loading station 14 to the probing station 16. A new meat cut C can be placed at the loading station 14 during this same period of time. FIG. 3D shows how the controller 116 further indexes the conveyor belt 22 after the above described description of the components in FIG. 3C. This causes the meat cut A to move to the cutting station 20; the door 121 opens to receive the meat cut C; and the meat cut B moves towards the waiting station 18. It should be noted that the controller also causes the lower horizontal portion 62 of belt 46 to engage the top meat product A as it moves into the cutting station (FIG. 3D). At the same time, the feedplate 126 engages the meal cut A and performs its boosting function of pushing the meat A through the skinning station as described heretofore.

Critical to the foregoing process is that the controller 116 receives a signal generated from fiber optics 112 to cause the blade 94 to cut the meat cut A passing through the skinning station 20 at a sufficient depth that the fat will be removed at a depth to expose at least six square inches of lean meat. The blade 94 will be at the appropriate depth by virtue of the measurements of sensor 102 transmitted to controller 116 and the encoder (not shown) to cause the blade 94 to be at a depth calculated by the controller. The controller carries out a calculation and transmits a signal to cause a cam shaft (not shown) to rotate within sleeves 88 causing blade arms 86 to adjust the height of blade holder 92 and blade 94 to a depth with respect to gripper roll 74 to cause the blade to be positioned at the correct height.

Description of an Alternate Embodiment

The preceding principal embodiment contemplates that the cutting blade 94 is moved to its designated cutting height in response to data from the probes, and remains in a stationary or constant position during the cut being made on the meat piece so probed. The alternative embodiment of the invention contemplates that the lateral attitude and/or the height may vary as the cut is being made so that the lateral and/or side profiles of the cut may vary during the cutting action.

The controller 116 (FIG. 2) can be loaded with profile cuts calling for varying blade heights during a given cut. These "memory" cuts are based on substantial historical data based upon a plurality of cuts of similar pieces of meat. Each cut A (FIG. 3A) is programmed to start with the blade 94 at approximately ⅛th inch in height. The probe 102 or sensor then signals the controller 116 as to the depth of cut the blade needs to make based upon the depth of fat that dwells below either the false lean layer 136, or the primary lean 138 (if there is no false lean). The controller 116 thereupon actuates the height adjustment mechanism of the blade and gradually raises the blade height as it proceeds through the longitudinally moving piece of meat. Thus, the blade will follow the cutting profile to an increased depth shown by the dotted line 140 in FIG. 12. Based upon historical data, the line 140 will be substantially horizontal as it approaches and passes the lower surface of false lean layer 136. The controller 116 knows to so control that center portion of line 140 because of data sensed by one or more probes 102. Again, based upon historical data, the controller causes the blade 94 to move from the horizontal plane of movement after the cut on line 140 moves beyond the false lean layer 136 to a deeper cut shown by the left hand end of cutting line 140 in FIG. 12. This terminal end 140A of line 140 is normally at the maximum cutting depth of the machine.

If more than one probe 102 is used to evaluate a single lab of meat, the controller 116 can adjust the height of the cutting blade 94 at more intervals along the cutting line 140. The ability of the blade 94 to have a varying cutting height during the cut on a given piece of meat, (as compared to the blade having a fixed height during such a cut) means that more fat can be eliminated by increasing the depth of cut in areas of thicker layers of fat, thus substantially increasing the yield of lean meat versus fat for each piece of meat.

FIGS. 7–10 show in more detail the blade holder 92 and blade 94 of FIG. 4. One end 92A of blade holder 92 is curved upwardly to accommodate the natural curve and thickness of a shoulder butt. On certain cuts of meat, greater amounts of fat can be trimmed if the blade holder and blade can have their opposite ends raised with respect to each other. The profile of the cutting blade from this perspective can also be imposed on the memory of a controller 116 to cause the tilting of the blade as shown in FIGS. 11 and 12. (See FIGS. 9 and 10.)

It is therefore seen that this invention will achieve at least all of its stated objectives.

What is claimed is:

1. A method for removing a portion of fat from meat cuts, comprising, placing a meat cut on a longitudinal conveyor, pressing at least one sensor probe into the meat cut to measure the thickness of fat and the location of lean in the meat cut, and then withdrawing the sensor probe from the meat, taking an electronic signal from the sensor probe and determining a depth from an outer lower surface of the meat cut through a layer of fat in the meat cut to a layer of lean in the meat cut, taking data from the preceding step and adjusting the position of a blade to a predetermined position with respect to the meat cut to remove a portion of fat from the meat cut to expose a given area of lean, cutting the portion of fat from the meat cut and varying the position of the blade while the cutting of the meat cut is taking place to optimize the amount of fat portion being removed, and the data is acquired by first optic fibers carrying light internally to the probes being pressed into the meat cut to emit light on an internal part of the meat cut into which the probe is being pressed, and second fiber optics in the probe to receive light from the first fiber optics that are reflected from the meat cut.

2. The method of claim 1 wherein the blade moves through a portion of fat wherein the thickness of cut of the blade in the meat cut increases at least in some portion of its cutting action.

3. The method of claim 1 wherein a controller receives the electronic signal and compares the data therefrom with historical data in a memory thereof to select a variable cutting path from a plurality of cutting paths in the memory to optimize amount of fat removed from the meat cut.

4. The method of claim 3 wherein the controller in response to signals from the sensor probe tilts the blade in a lateral plane with respect to a longitudinal axis of the conveyor to further optimize the removal of fat from the meat cut.

5. The method of claim 3 wherein a plurality of sensor probes provide signals to the controller to determine the varying position of the blade while fat is removed from a meat cut.

6. An apparatus for removing a portion of fat from meat cuts, comprising, a frame, at least one sensor probe having an elongated probe spike and including fiber optics to permit scanning of the interior of a meat cut penetrated by the probe spike, a probing station on the frame, means for moving the probe spike of the sensor probe into and out of a meat cut at the probing station, an elongated skinning blade mounted on the frame, a control on the frame operationally connected to the sensor probe for receiving data from the sensor probe to determine the linear thickness of fat exterior material on the meat cut, means on the control for evaluating the data to determine the variable operating positions of the blade to effect the removal from the meat cut of a predetermined amount of fat, and for variably moving the blade through the variable operating positions while the apparatus is removing a portion of fat from the meat cut.

7. The apparatus of claim 6 wherein a control on the frame receives an electronic signal and compares the data therefrom with historical data in a memory thereof to select a variable cutting path from a plurality of cutting paths in the memory to maximize amount of fat removed from the meat cut.

8. The apparatus of claim 6 wherein a plurality of sensor probes provide signals to the controller to determine the varying height of the blade while fat is removed from a meat cut.

9. The apparatus of claim 6 wherein the blade is elongated and its variable operating positions involving changing the relative elevations of opposite ends of the blade.

10. The apparatus of claim 6 further comprising a conveyor operatively associated with the frame.

11. The apparatus of claim 10 wherein the control in response to signals from the sensor probe tilts the blade in a lateral plane with respect to a longitudinal axis of the conveyor to further maximize the removal of fat from the meat cut.

12. The apparatus of claim 10 wherein the variable operating positions of the blade involves a range of height variations of the blade with respect to the conveyor.

13. The apparatus of claim 10 wherein the skinning blade is mounted in a curved blade holder attached to a shoe assembly at a skinning station, a blade height adjusting mechanism on the frame operatively connected to a control mechanism, and a gripper roll and shoe assembly on the frame adjacent the skinning blade, and the conveyor engageable with a meat cut at the skinning station to hold the meat cut in a constant orientation while being moved through the skinning station so that the depth of cut is consistent with the depth measured by the probe.

\* \* \* \* \*